(12) United States Patent
Gonzales et al.

(10) Patent No.: US 6,837,871 B2
(45) Date of Patent: Jan. 4, 2005

(54) SELF-DEPLOYING CATHETER ASSEMBLY

(75) Inventors: Joseph A. Gonzales, Tehachapi, CA (US); Boun Pravong, Corona, CA (US)

(73) Assignee: Applied Medical Resources, Santa Margarita, CA (US)

( * ) Notice: Subject to any disclaimer, the term of this patent is extended or adjusted under 35 U.S.C. 154(b) by 52 days.

(21) Appl. No.: 10/403,758

(22) Filed: Mar. 31, 2003

(65) Prior Publication Data

US 2003/0167069 A1 Sep. 4, 2003

Related U.S. Application Data

(63) Continuation-in-part of application No. 09/870,255, filed on May 30, 2001, now Pat. No. 6,589,208.
(60) Provisional application No. 60/260,794, filed on Jan. 9, 2001, and provisional application No. 60/212,912, filed on Jun. 20, 2000.

(51) Int. Cl.[7] ............................................. A61M 37/00
(52) U.S. Cl. .................................... 604/104; 604/96.01
(58) Field of Search ................................ 604/104, 107, 604/96.01, 99.01, 102.01, 177; 606/232, 191, 192, 198

(56) References Cited

U.S. PATENT DOCUMENTS 6,558,350 B1 * 5/2003 Hart et al. .................. 604/104

* cited by examiner

*Primary Examiner*—Henry Bennett
(74) *Attorney, Agent, or Firm*—Richard L. Myers; Kenneth K. Vu

(57) ABSTRACT

A catheter having an elongate drainage tube with a proximal end and a distal end, is adapted to extend through a body conduit and into a body cavity. An anchor disposed the distal end of the tube is disposed in the body cavity and is adapted to be moved from an insertion position to a withdrawal position. The anchor in the insertion position has a low profile when the tube is moved distally and in the withdrawal position has a low profile when the tube is moved proximally. The first end of the anchor is attached to the tube, and a tension member is provided to extend distally of the tube to releasably hold the second end of the anchor in a fixed relationship with the tube. In an associated method, this tension member is severed to release the second end of the anchor from the tube and permit withdrawal of the tube and the anchor in a low-profile state.

13 Claims, 10 Drawing Sheets

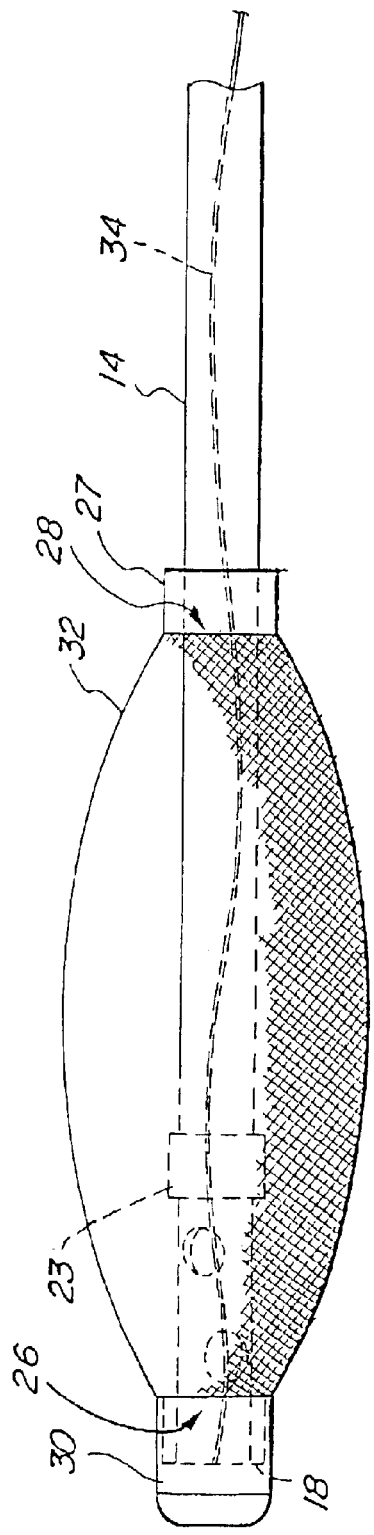
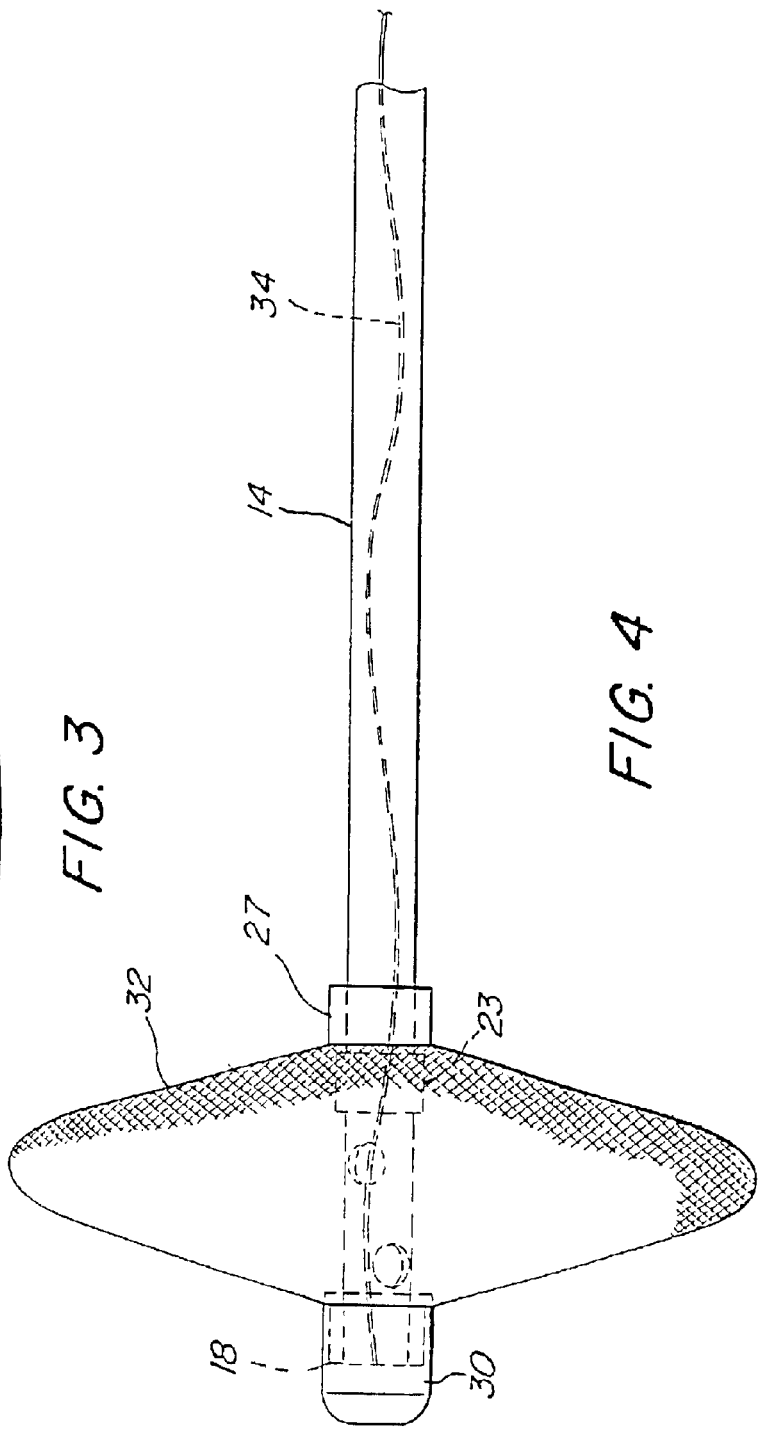

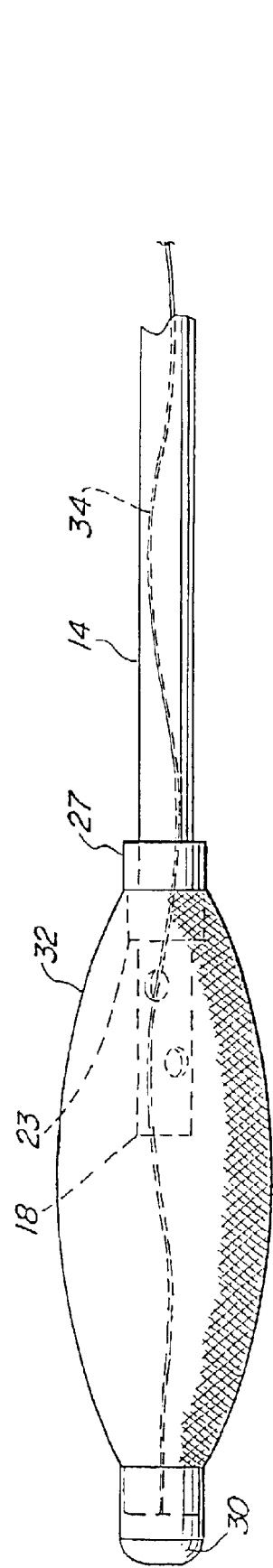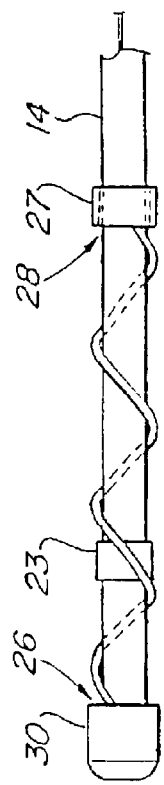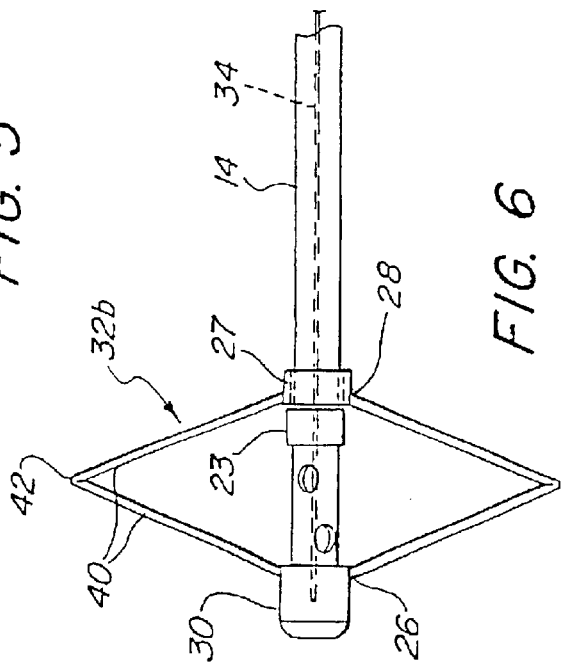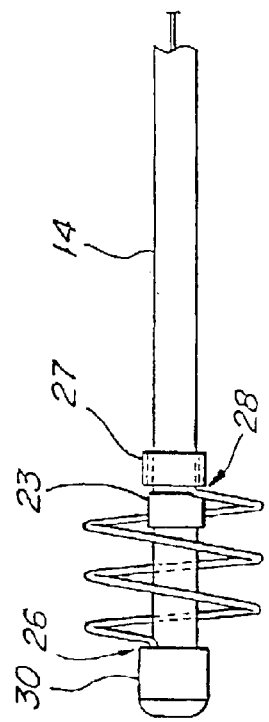
FIG. 5
FIG. 7
FIG. 8
FIG. 6

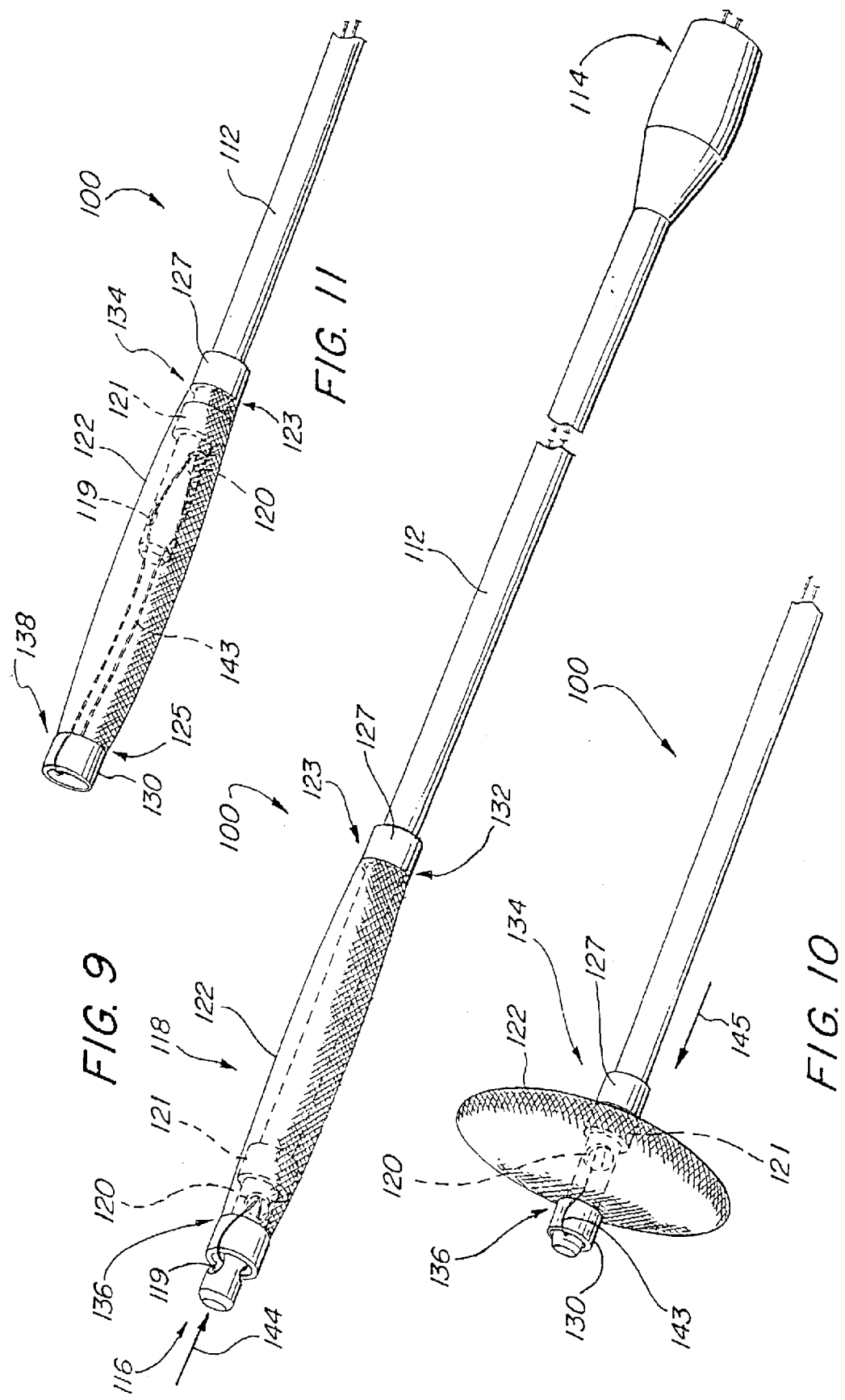

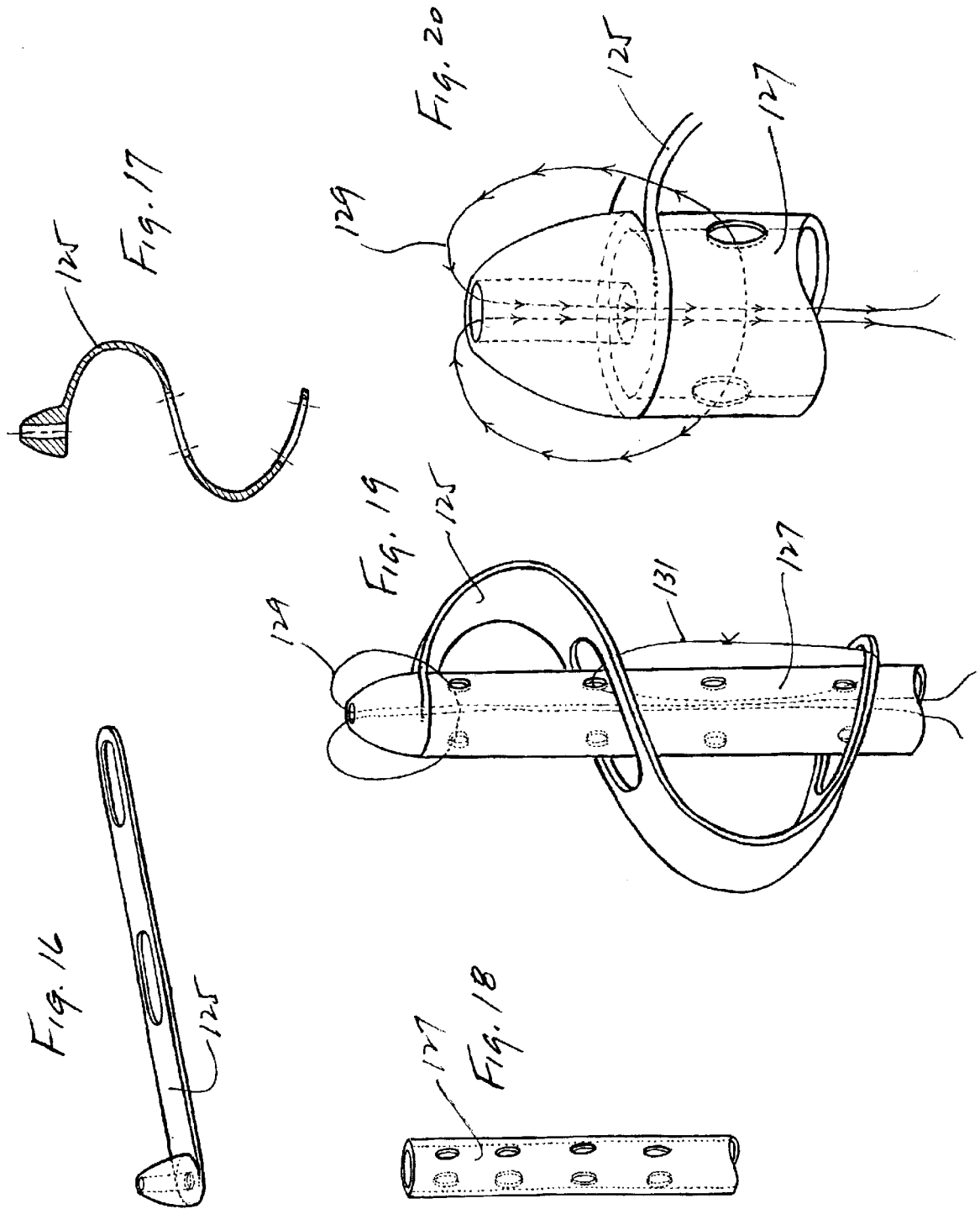

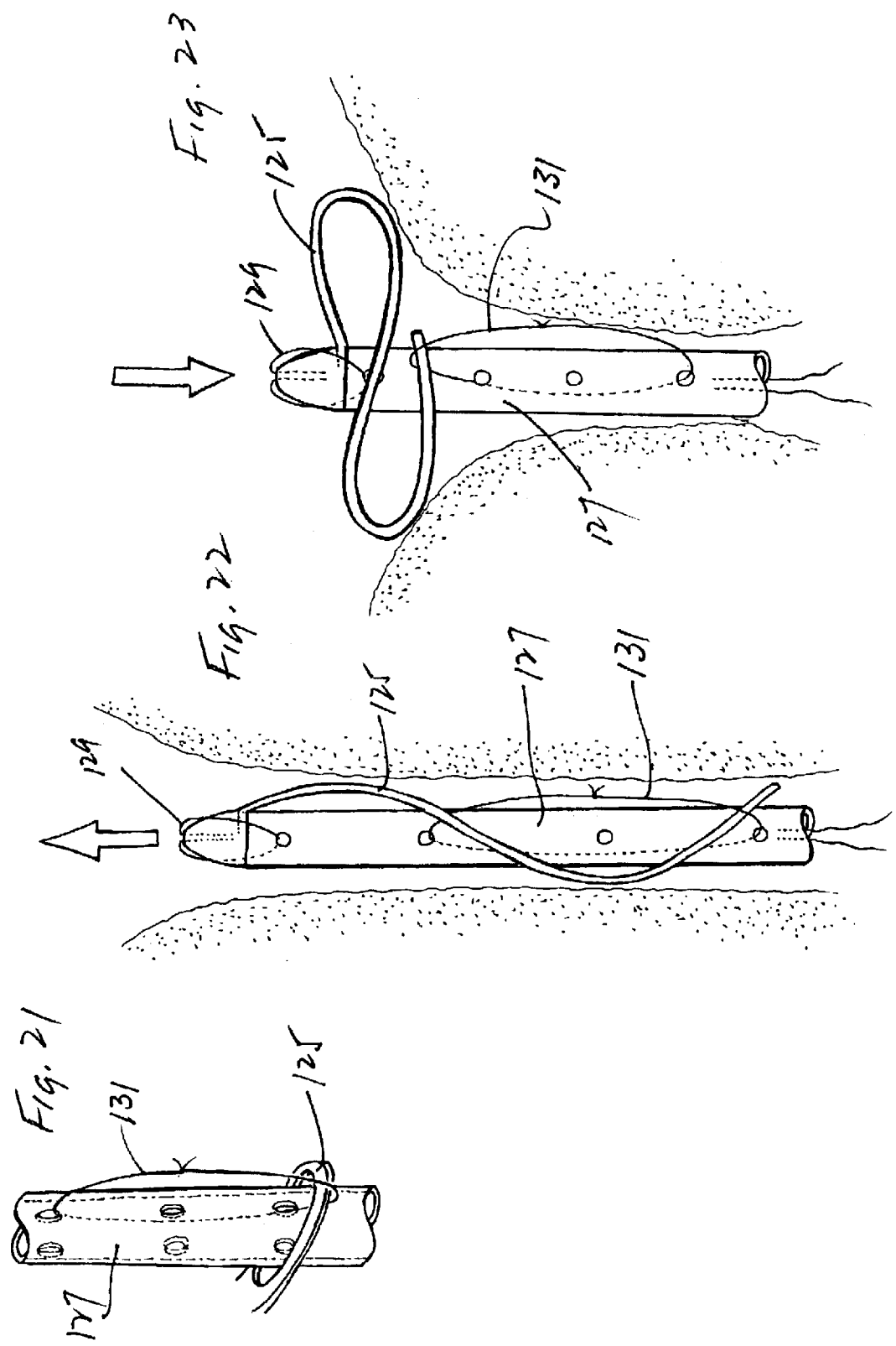

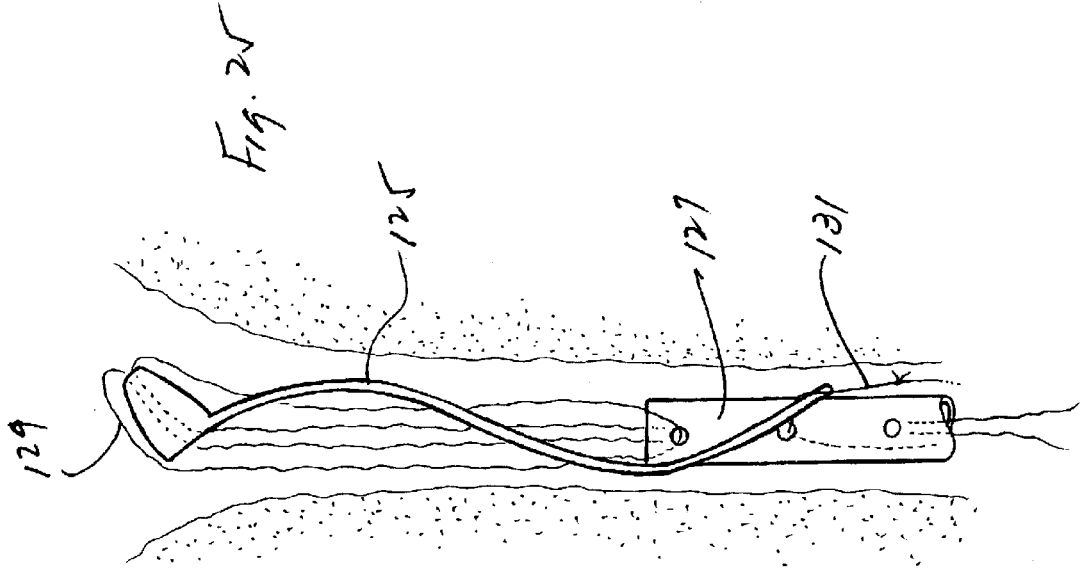
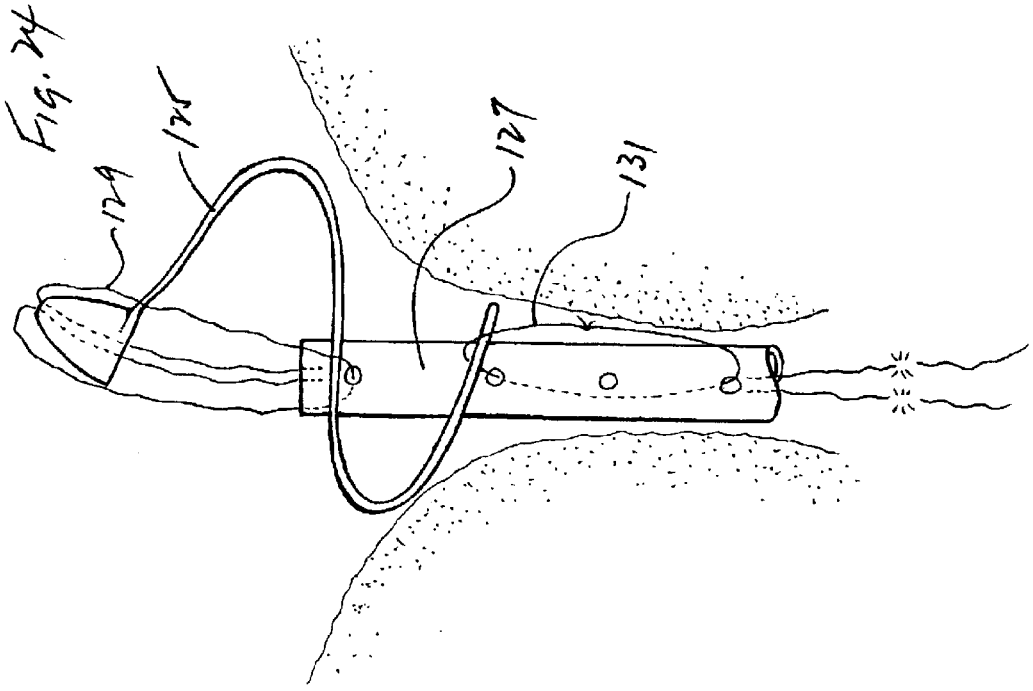

SELF-DEPLOYING CATHETER ASSEMBLY

CROSS REFERENCE TO RELATED APPLICATIONS

This application relates to and claims priority from U.S. Provisional Application Ser. No. 60/212,912 entitled SELF-DEPLOYABLE DRAINAGE CATHETER filed on Jun. 20, 2000, and U.S. Provisional Application Ser. No. 60/260,794 entitled ANCHORING ASSEMBLY FOR MEDICAL INSTRUMENT filed on Jan. 9, 2001, and continuation-in-part U.S. application Ser. No. 09/870,255 filed on May 30, 2001, now U.S. Pat. No. 6,589,208 entitled SELF DEPLOYING CATHETER ASSEMBLY, each of which is incorporated herein by reference.

BACKGROUND OF THE INVENTION

1. Field of the Invention

The present invention relates generally to medical and surgical devices, and more specifically to catheter assemblies.

2. Description of Prior Art and Related Information

Catheter assemblies are generally inserted through body conduits to provide access to body cavities so as to enable medical procedures to be performed less invasively. In certain procedures, such as surgery or drainage, it is necessary for the catheter to be temporarily anchored in the body cavity to allow the desired procedure to be completed.

Different mechanisms have been provided for the purpose of deploying a catheter within a body cavity in order to prevent withdrawal during a procedure. One example includes an inflatable balloon disposed on the tip of a catheter. Once the tip is within the body cavity, the balloon is inflated through an inflation lumen running through the shaft of the catheter. The presence of the inflation lumen, however, increases the necessary diameter of the shaft which must also accommodate a second lumen intended for the desired procedure, such as a drainage lumen.

A larger catheter diameter, however, increases discomfort. While decreasing the diameter of the inflation lumen may contribute to a slightly smaller overall diameter of a catheter, an inflation lumen with a small diameter is more likely to develop kinks in the passageway, obstructing the flow of fluid necessary to inflate and deflate the balloon.

Conventional balloons are not liquid permeable. In drainage procedures, therefore, ports must be provided in the shaft at a location outside of the balloon. In typical catheters where ports are disposed on the shaft proximate to the balloon, a greater length of the catheter must be inserted into the body cavity in order to provide fluid communication between the ports and the liquid within the cavity. This greater "stack profile: increases discomfort. Furthermore, particular body cavities can only accommodate a certain length of catheter. Therefore, limited room is available for the placement of ports on the shaft, which leads to a small overall area for drainage. This smaller area contributes to excessive residual liquid remaining in the body cavity which may lead to infections and other complications.

Conventional catheters, including balloon catheters, must be manually deployed. Thus, an operator must gauge when the tip portion of the catheter, including the balloon, is sufficiently within the target body cavity in order to initiate inflation. Predilation, resulting in severe trauma to the patient, can occur if the deploying device, such as a balloon, is prematurely expanded in the narrow body conduit connected to the cavity.

The removal of conventional catheters is also problematic because manual manipulation is required. A typical anchor, such as a balloon, deployed in the body conduit is configured in its expanded, high-profile state. Before the catheter may be withdrawn, the conventional anchor must be manually returned to its low-profile state so that it may re-enter the narrow body conduit. Various mechanisms are provided in the prior art for manually converting the anchor from its high-profile state to its low-profile state. One existing method includes inserting a stylet through the catheter to push the distal tip out in order to form the low-profile state. The necessity for manual manipulation in conventional assemblies increases time, effort, expense and inconvenience in withdrawing a catheter.

SUMMARY OF THE INVENTION

The present invention provides structures and methods which overcome the deficiencies of the prior art.

In one aspect, a method is provided for inserting a medical instrument through a body conduit and for anchoring the medical instrument in a body cavity. The method comprises the steps of providing an elongate tube having a shaft proximal end and a shaft distal end, affixing a stop along the tube at an anchoring position, forming an anchoring device with an anchor proximal end and an anchor distal end, providing the anchoring device with characteristics including a high-profile state when the anchor proximal end and the anchor distal end are in a generally proximate relationship, and a low-profile state when the anchor proximal end and the anchor distal end are in a generally spaced relationship, and mounting the anchoring device relative to the tube with the anchor distal end movable between a distal end proximal position distal of the stop and a distal end distal position, and with the anchor proximal end movable between a proximal end proximal position and a proximal end distal position proximal of the stop.

The method also comprises the steps of inserting the tube into the body conduit toward the body cavity, and during the inserting step, moving the anchor proximal end to the proximal end proximal position with the anchor distal end at the distal end proximal position to maintain the anchoring device in the low-profile state. The method further comprises the steps of positioning the tube with the stop in the body cavity, and withdrawing the tube sufficiently to move the anchor proximal end to the proximal end distal position and to provide the anchoring device with its high profile characteristics.

The step of withdrawing the tube comprises the step of moving the anchor proximal end to the proximal end distal position within the body cavity. The method further comprises the step of releasably locking the distal end of the anchoring device in the distal end proximal position, retracting the shaft from the body cavity, during the retracting step, releasing the anchor distal end from the distal end proximate position; and, after the releasing step, moving the anchor distal end to the distal end distal position to space the anchor distal end from the anchor proximal end so as to provide the anchoring device with its low-profile characteristics during the retracting step.

The releasably locking step comprises the step of coupling the anchor distal end to a suture engaged in a proximal direction. The releasing step comprises the step of disengaging the suture from the proximal direction. The step of forming an anchoring device comprises the step of forming a bulb, the step of forming a hinged wing structure, or the step of forming a spiral. The method further comprises the step of draining fluid from the body cavity with the anchoring device and the tube.

In another aspect, a method is also provided for inserting a catheter assembly through a body conduit and automatically deploying the assembly into a body cavity. The method comprises the steps of coupling an anchoring device with an anchor proximal end and an anchor distal end to a tube, providing the anchoring device with characteristics ranging between a high-profile state when the anchor proximal end and the anchor distal end are in a generally proximate relationship, and a low-profile state when the anchor proximal end and the anchor distal end are in a generally spaced relationship, disposing a stop on the tube between the anchor proximal end and the anchor distal end, automatically forming the low-profile state upon inserting the anchoring device into the body cavity, and automatically forming the high-profile state upon withdrawing the tube with the anchoring device disposed in the body cavity.

The step of automatically forming the low-profile state comprises the step of forming the low-profile state only by inserting the tube in a distal direction. The step of automatically forming the high-profile state comprises the step of forming the high-profile state only by moving the tube in a proximal direction once the anchoring device is disposed in the body conduit without any manual manipulation of the anchoring device.

Once the anchor distal end is disposed in the body cavity, the method further comprises the step of moving the anchor distal end from a distal end proximal position adjacent to the stop to a distal end distal position further from the stop to facilitate a low-profile state for removal of the anchoring device. The step of moving the anchor distal end from the distal end proximal position to the distal end distal position comprises the step of releasing a lock adapted to hold the anchor distal end in the distal end proximal position.

An anchor assembly movable with a medical device through a body conduit is provided for anchoring the medical device in a body cavity. The assembly comprises an elongate tube associated with the medical device and having a shaft proximal end and a shaft distal end, a stop fixed to the tube generally at a position desired for anchoring the tube, an anchoring device carried by the tube and having an anchor distal end distal of the stop, and an anchor proximal end proximal of the stop. The distal end of the anchoring device is movable between a distal end proximal position and a distal end distal position. The anchor proximal end is movable between a proximal end proximal position and a proximal end distal position. The assembly also includes a lock operable from the shaft proximal end to hold the anchor distal end in the distal end proximal position to facilitate insertion in the low-profile state and anchoring in the high-profile state. The lock is operable to release the anchor distal end from the distal end proximal position to facilitate withdrawal of the medical instrument with the anchoring device in the low-profile state.

In a preferred embodiment, the anchoring device comprises a bulb composed of a liquid permeable material. The tube comprises apertures disposed at a position between the proximal end and the distal end of the anchoring device.

In a further aspect, a self-deployable catheter assembly is provided. The assembly comprises a tube with a shaft proximal end and a shaft distal end, a stop fixed to the tube at a stop position between the shaft proximal end and the shaft distal end, an anchoring device carried by the tube, and a releasable lock operable to hold the anchor distal end in a distal end proximal position to facilitate insertion in the low-profile state and anchoring in the high-profile state. The anchoring device has an anchor distal end distal of the stop, and an anchor proximal end proximal of the stop. The anchoring device is movable between a low-profile state and a high-profile state. The lock is operable to release the anchor distal end from the distal end proximal position to facilitate withdrawal in the low-profile state.

The anchoring device may comprise a bulb, a hinged wing structure, a spiral, or any other structure that is interchangeable between an expanded, high-profile state and a narrow, low-profile state.

The anchor proximal end is freely movable between a proximal end distal position adjacent to the stop, and a proximal end position spaced apart from the stop. A slide is coupled to the anchor proximal end. A slidable bushing or cap is coupled to the anchor distal end. The releasable lock preferably comprises a suture.

In a further aspect, a catheter assembly is provided, comprising a tube; and an anchoring device mounted to the tube. The anchoring device has an anchor distal end held in a fixed position by a releasable lock and an anchor proximal end freely movable between a proximal end proximal position and a proximal end distal position. The proximal end distal position is defined by a stop disposed on the tube between the anchor distal end and the anchor proximal end. The anchoring device has a high-profile state when the anchor distal end and the anchor proximal end are in a generally proximate relationship, and a low-profile state when the anchor distal end and the anchor proximal end are in a generally spaced relationship. The distal end is movable to a released position distal of the fixed position upon releasing the lock. The anchoring device may be liquid permeable. The tube comprises apertures disposed between the anchor proximal end and the anchor distal end.

Another drainage catheter of particular interest includes an anchor having a distal end and a proximal end. The anchor is formed from thermoset or heatset material in the configuration of a strap bendable to an S-shape. A catheter shaft is threaded through large slots in this strap and joined to the distal tip of the strap by a suture material which is threaded back through the catheter shaft. A separate piece of suture material attaches the proximal end of the strap to the catheter shaft. The ease and simplicity of this construction contributes to low cost manufacture of the device without sacrificing any of the advantages appreciated in the prior art. The catheter is easily inserted, provides a substantial anchor structure and is simply and easily removed by merely cutting the suture material to separate the distal tip of the strap from the catheter shaft.

In several of these embodiments, it will be noted that an anchoring device comprises both an anchor distal end and an anchor proximal end, the proximity of which determine whether the anchoring device has a high or low profile. Thus, these opposed ends facilitate both a high-profile state when close together in a proximate relationship, and a low-profile state when spaced further apart in a spaced relationship. It will further be noted that the anchor distal end is held in a distal end proximal position by a releasable lock that is operative from the time the catheter is manufactured until the time the lock is released. Once the lock is released, the anchor distal end is movable to the distal end distal position.

In summary, a self-deploying catheter assembly comprises an anchoring device mounted to a tube. A distal end of the anchoring device is held in a fixed position by a releasable suture while a proximal end is freely movable between a proximal position and a distal position defined by a stop on the tube. During insertion into a body cavity, the anchor automatically maintains a low-profile state with the ends spaced apart. Once fully inserted, the anchor self converts into a high-profile state when the tube is slightly withdrawn, bringing the ends closer together. The suture is disengaged to release the distal end of the anchor in order to facilitate a low-profile state for withdrawal of the assembly.

The invention, now having been briefly summarized, may be better appreciated by the following description of preferred embodiments and reference to the associated drawings.

DESCRIPTION OF THE DRAWINGS

FIG. 3 is a side elevation view of the first preferred catheter assembly in a low-profile state;

FIG. 4 is a side elevation view of the first preferred catheter assembly in the high-profile state;

FIG. 5 is a side elevation view of the first preferred catheter assembly in a released, low-profile state.

FIG. 6 is a side elevation view of a second embodiment of a catheter assembly in a high-profile state;

FIG. 7 is a side elevation view of a third embodiment of a catheter assembly in a low-profile state;

FIG. 8 is a side elevation view of the third embodiment of a catheter assembly in a high-profile state;

FIG. 9 is a perspective view of a fourth embodiment of a catheter assembly in a low-profile state;

FIG. 10 is a perspective view of the fourth embodiment of a catheter assembly in a high-profile state;

FIG. 11 is a perspective view of the fourth embodiment of a catheter assembly in a released, low-profile state

FIG. 16 is a perspective view of an embodiment of an anchor which is formed as a strap, and illustrated in a straight configuration;

FIG. 17 is a perspective view of a catheter shaft with drainage holes;

FIG. 18 is a side elevation view showing a catheter shaft with the anchor strap sutured through the drainage holes;

FIG. 19 is an enlarged perspective view of the anchor strap sutured to the catheter shaft;

FIG. 20 is a side elevation view illustrating attachment of the proximal end of the strap to the catheter shaft;

FIG. 21 is a perspective view illustrating a step of inserting the catheter with anchor strap;

FIG. 22 is a perspective view illustrating the deploying of the anchor strap;

FIG. 23 is a perspective view illustrating the cutting of sutures to release the distal tip of the strap from the catheter shaft;

FIG. 24 is a perspective view illustrating removable of the catheter shaft along with the separated anchor strap; and FIG. 25 is an enlarged perspective view of the removal step illustrated in FIG. 24.

DESCRIPTION OF PREFERRED EMBODIMENT AND BEST MODE OF THE INVENTION

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

Figure 1:
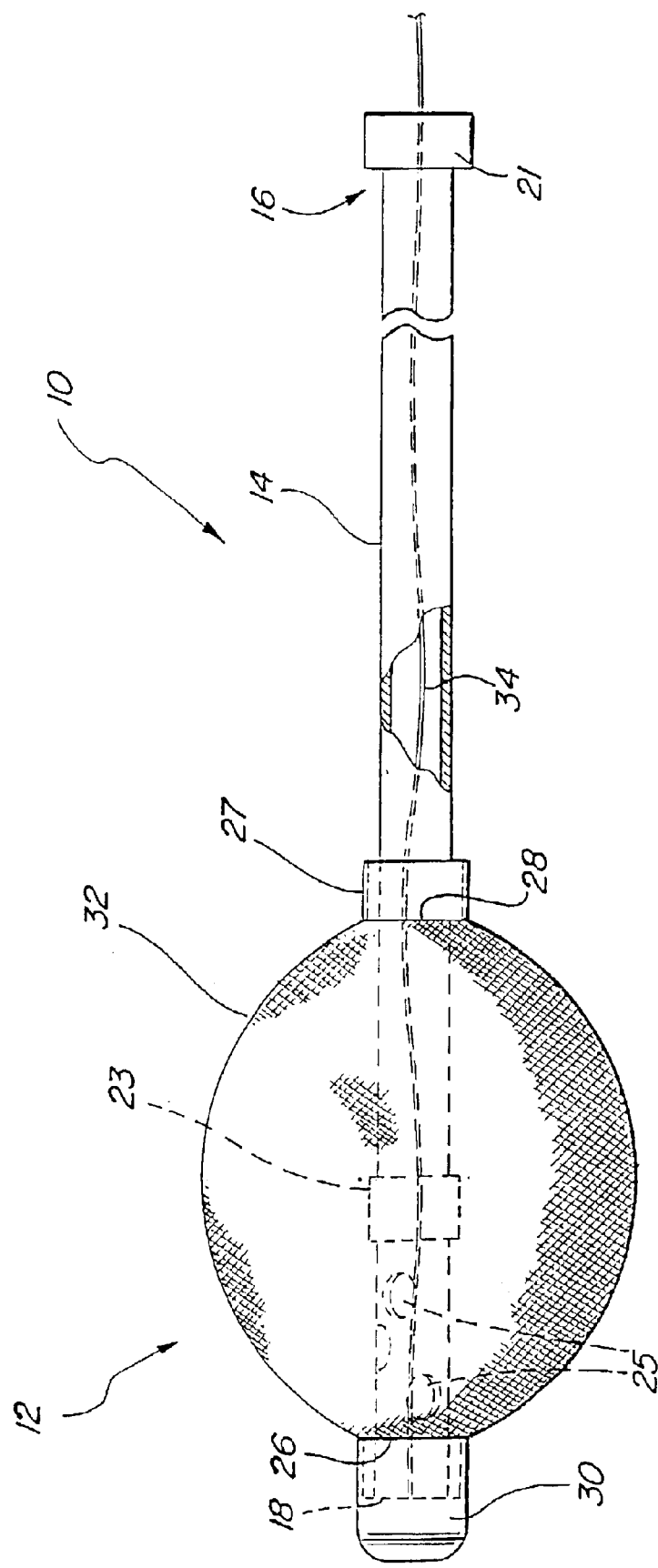
FIG. 1 is a side elevation view of a first preferred catheter assembly according to the invention.
Figure 2:
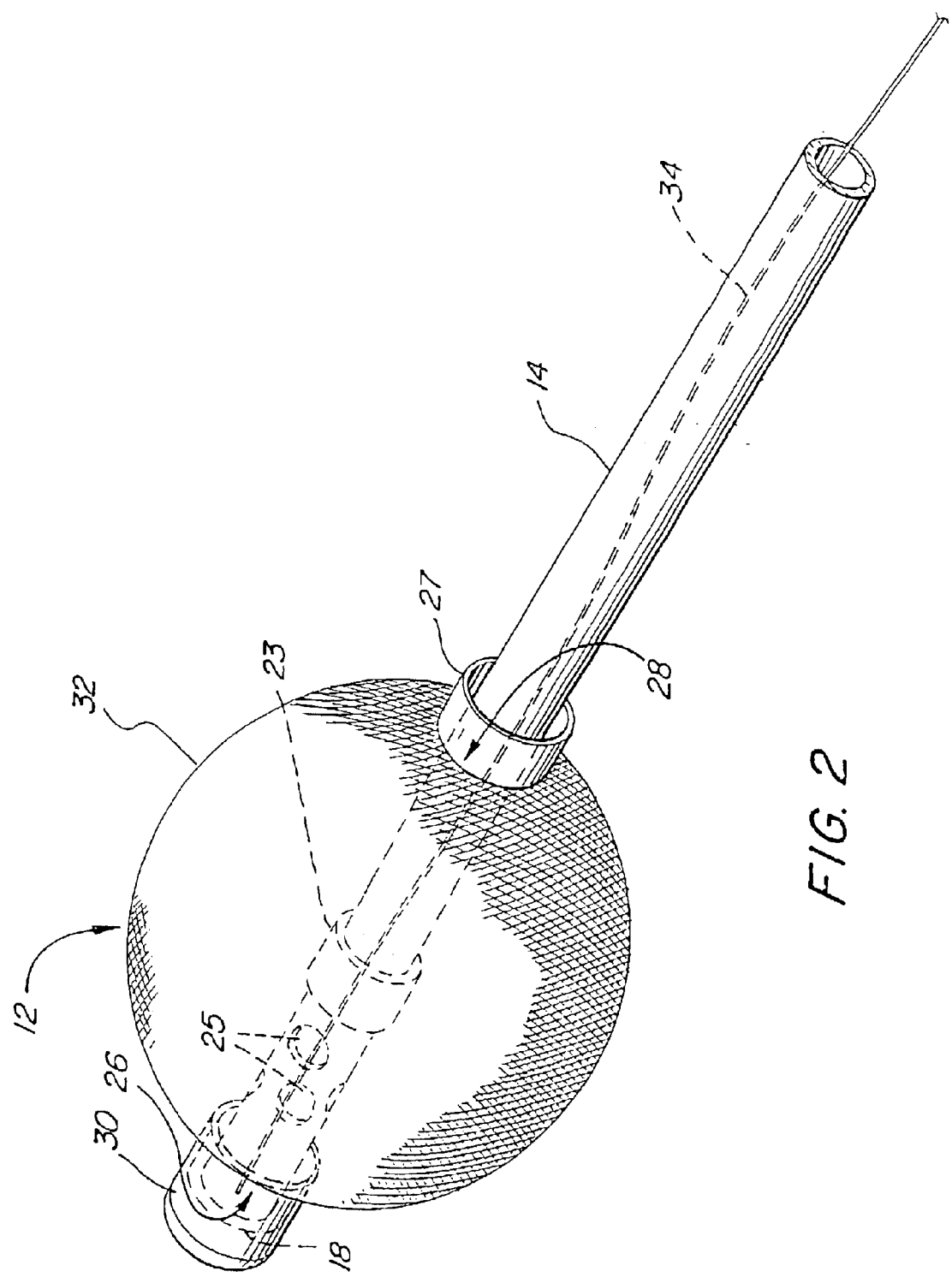
FIG. 2 is a perspective view of the first preferred catheter assembly in a high-profile state.

A first preferred embodiment of a catheter assembly is illustrated in FIG. 1 and designated generally by the reference numeral 10. This catheter assembly, or simply catheter 10, has a self-deploying tip, or anchor assembly 12, which can be advantageous in many catheter configurations. In FIGS. 1 and 2, the catheter 10 is adapted for urinary drainage where the anchor assembly 12 facilitates insertion of the catheter 10, automatic deployment of the tip 12, and simple removal of the catheter 10. Other catheters which can benefit from the serf-deployment properties of the anchor assembly 12 include occlusion catheters, and generally any catheter in which the properties of minimal insertion force, maximum anchor force, and a simple release mechanism would be advantageous.

Although the catheter assembly 10 may be particularly adapted for drainage, it is to be expressly understood that the catheter assemblies according to the invention may be employed in any medical procedure in which a catheter is required to be inserted through a body conduit and anchored in a body cavity. The conduits could be a naturally occurring body conduit, such as a urethra, or an artificially created conduit such as those created in nephrostomy. Therefore, the catheter assemblies according to the invention may be employed, for example, in surgical procedures, drainage procedures, infusion procedures, feeding procedures, nephrostomy, gastronomy and more.

The catheter 10 may include an elongate tubular body, or shaft, 14 having a shaft proximal end 16 and a shaft distal end 18. A hub 21 will commonly e fixed to the tubular body 14 at the shaft proximal end 16. Near the shaft distal end 18, a stop 23 may be provided to form an enlargement on the outer surface of the tubular body 14. The position of the stop 23 is fixed at this stop location on the tubular body 14. Between the shaft distal end 18 and the stop 23, the walls of the tubular body 14 can be perforated to form drainage ports, or apertures, 25, which provide access from regions exterior of the catheter 10 into the lumen of the tubular body 14.

The stop 23 forms part of the anchoring assembly 12 which provides the catheter 10 with its self-deploying tip configuration. This anchoring assembly, 12 may also include a bushing or slide 27 which is free to slide on the tubular body 14, but only proximally of the stop 23. Thus, the stop 23 inhibits distal movement of the slide 27 along the tubular body 14. The self-deployment mechanism also includes a distal cap 30 which is movable relative to the body 14 between a first position in proximity to the shaft distal end 18, and a second position wherein it is spaced distally of the distal end 18.

In other embodiments, the cap 30 could also function as a sliding bushing, such as the bushing 27, and have its own stop, such as the stop 23. In such an embodiment, the distal tip 18 of the tube 14 would not be capped, as in the illustrated embodiment, but would extend through both bushings. In FIG. 1, the shaft distal end 18 actually functions as a stop for the cap 30 as it inhibits proximal movement of the cap 30 along the tubular body 14.

An anchoring device 32 has an anchor distal end 26 fixed to the cap 30 and an anchor proximal end 28 fixed to the slide 27. The stop 23 is thus disposed on the shaft 14 between the anchor distal end 26 and the anchor proximal end 28 of the anchoring device 32. In the pre4ferred embodiment, the anchoring device 32 comprises a bulb. The bulb 32, which can be formed of any biocompatible flexible material, can be provided with special characteristics facilitating drainage. Thus, in the illustrated embodiment, the bulb 32 is formed of a heat-settable material, such as polyester, and provided in the configuration of an open mesh so as to be liquid permeable. In the case of a drainage catheter, the apertures 25 may be defined in the tube 14 such that they are located in an interior of the liquid permeable bulb 32 between the opposed anchor ends 26, 28.

The anchoring device 32 has a high-profile state and a low-profile state, each of which is dependent upon the relative positions of the anchor distal end 26 and the anchor proximal end 28. Since the distal end 26 and proximal end 28 are coupled to the slide 27 and the cap 30, respectively, the state of the anchoring device's profile is also determined by the relative positions of the slide 27 and cap 30. Thus, when the slide 27 and cap 30 are in close proximity, as in a proximate relationship, the anchor proximal end 28 and anchor distal end 26 are closely spaced providing the anchoring device 32 with a high-profile, expanded configuration. When the slide 27 and cap 30 are widely spaced, as in a spaced relationship, the anchor proximal end 28 and anchor distal end 26 are more separated to provide the anchoring device 32 with a low-profile, narrow configuration.

The relative movement of the slide 27 and cap 30 coupled to the anchor proximal end 28 and anchor distal end 26 of the anchoring device 32, respectively, provides the self-deployment characteristics associated with the present invention. The only additional structure which may be required for this mechanism is a simple releasable lock 34, such as a suture, tube, string or other releasable tension member, which can be fixed to the cap 30 and threaded back through the lumen of the tubular body 14.

In operation, the strong 34 tensions the cap 30 in a proximal direction and holds it against its stop, such as the shaft distal end 18 of the tube 14. In this tensioned state, the string 34 can be manufactured so that its proximal end is maintained in a fixed relationship with the tube 14. In a preferred embodiment, the proximal end of the string 34 is fixed to the hub 21. Distally of the hub 21, or any other point of fixation to the tubular body 14, the string 34 is under tension, but not attached to the tubular body 14.

In this manufactured state, it can be seen that the cap 30 is maintained in its proximal position in a fixed relationship with the tube 14. Since the cap 30 couples the releasable lock 34 to the anchor distal end 26, the releasable lock 34 also tensions the anchor distal end 26 in a proximal direction, thereby holding the anchor distal end 26 in a distal end proximal position.

Figure 12:
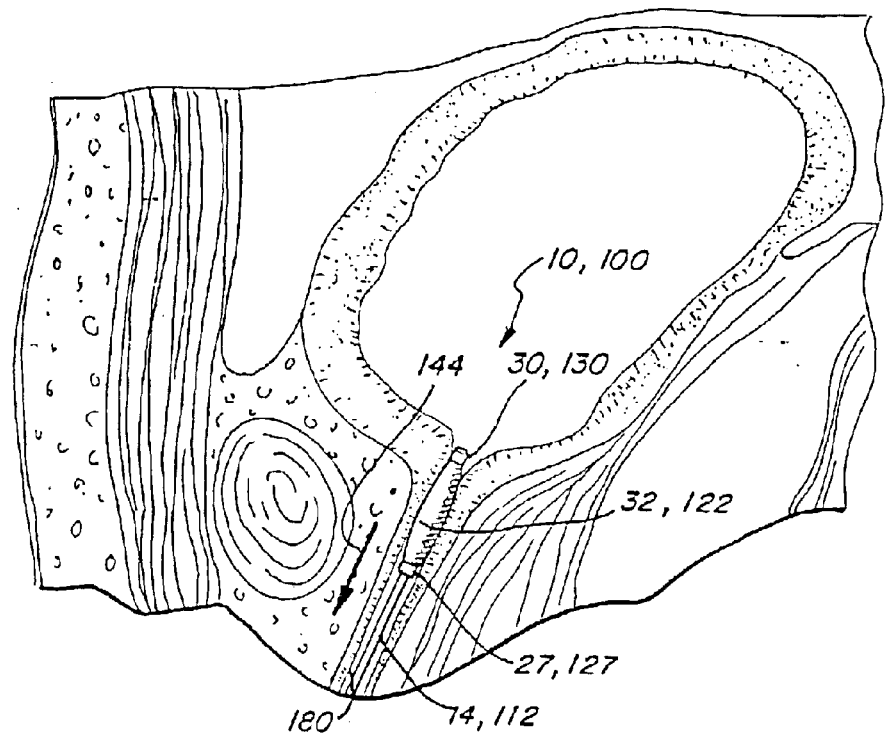
FIG. 12 is a schematic view of a catheter assembly of the present invention operatively disposed in a body conduit leading to a body cavity.

By comparison, it will be noted that the anchor proximal end 28 and corresponding slide 27 at the opposite end of the anchoring device 32 is free to move along the tube 14 proximally of the stop 23. These characteristics greatly facilitate insertion of the catheter 10 with the anchoring device 32 in a low-profile state, as illustrated in FIG. 3. Insertion forces, which are exerted against the anchoring device 32 in a proximal direction, as shown in FIG. 12, tend to force the anchoring device 32 into a low-profile state, which is easily accommodated by movement of the anchor proximal end 28 and slide 27 proximally along the tube 14. With the cap 30 already in its proximal-most position against the stop or distal end 18, it is not free to move in response to these insertion forces, thereby maintaining the anchor distal end 26 in the distal end proximal position. It will be appreciated that no external forces are required of the user in order to maintain the anchoring device 32 in the low-profile state during insertion. The anchoring device 32 automatically self-deploys to this low-profile state with a simple, one handed insertion force applied to the tubular body 14 without any further manual manipulation.

In the case of a urinary drainage catheter, the catheter 10 is inserted through the urethra and past a bladder neck as it enters the bladder. Once the anchoring device 32 is inside the bladder, it is no longer constrained by the walls of the urethra to the low-profile state. By forming the bulb 32 of a heat-settable material, it can be heat-set to an enlarged profile, so that it automatically expands slightly within the bladder. The self-deployment characteristics of this invention are particularly apparent at this point in the process, where it is intended that the distal end of the catheter 10 will be anchored within the bladder to facilitate the drainage of urine. This anchoring is automatically achieved by the slight withdrawal of the tube 14 proximally.

Figure 14:
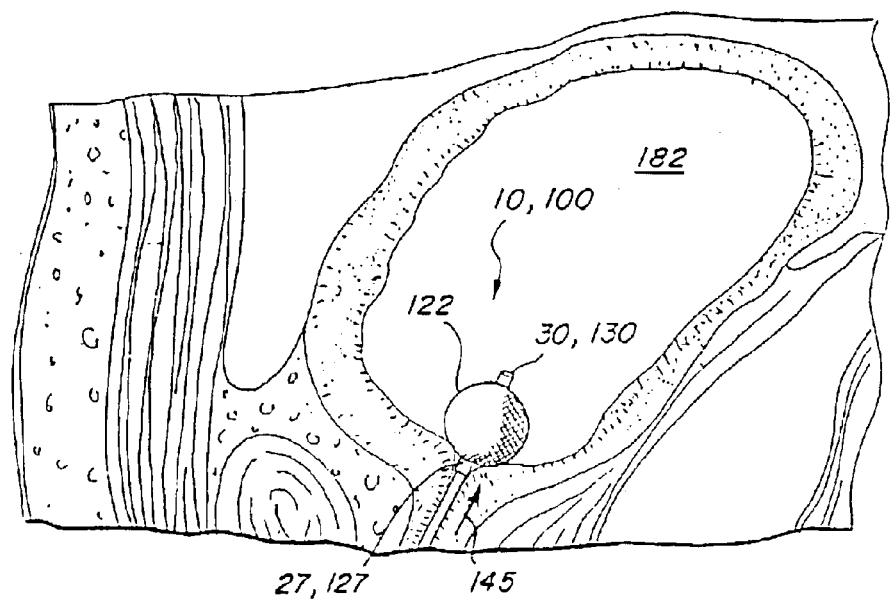
FIG. 14 is a schematic, operational view of the catheter assembly illustrating the self-deploying feature of the anchoring device upon slight withdrawal of the shaft.

Initially, this withdrawal force brings the slide 27 and the anchor proximal end in contact with the bladder neck, as shown in FIG. 14. At this point, the withdrawal force pushes distally against the slide 27, causing it and the anchor proximal end to move distally to the stop 23, as illustrated in FIG. 4. Due to tension on the string 34, the cap 30 and anchor distal end 26 are not free to move distally in response to these withdrawal forces, but, instead, are held in this fixed, distal end proximal position. Accordingly, a slight withdrawal force brings the two ends 26, 28 of the anchoring device 32 into close proximity and causes the anchoring device 32 to achieve its greatest radius in the high-profile state, illustrated in FIGS. 4 and 14.

At this point, it can be seen that any proximal force tending to withdraw the catheter 10 will only seek to maintain the enlarged high-profile state, which anchors the catheter 10 within the body cavity. It will be further noted that, up to this point in the process, the tube 14 has merely been pushed forward slightly to facilitate insertion and then pulled backward slightly to lock the anchoring device 32 in its high-profile state. Deployment of the anchoring device 32 initially to the low-profile state and ultimately to the high-profile state has required no further action or force on the part of the user.

Figure 15:
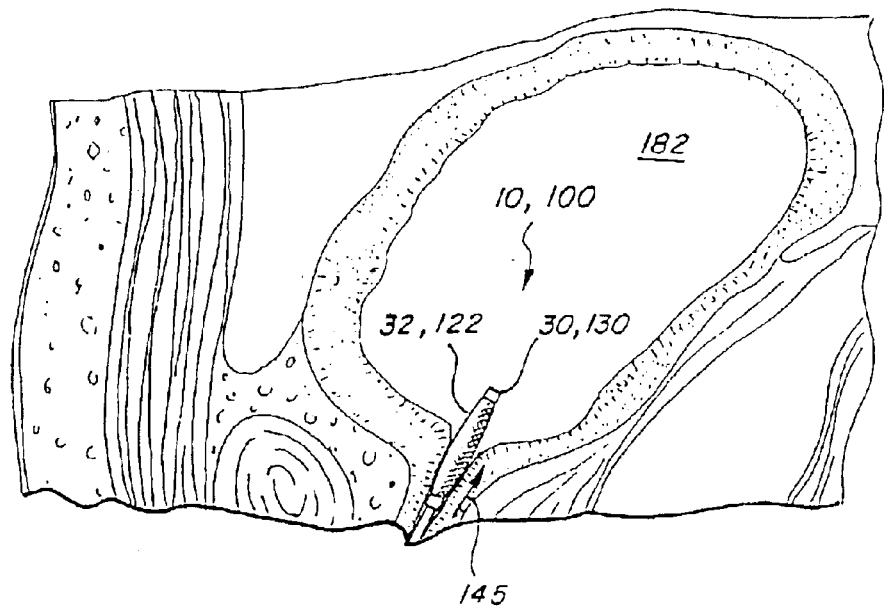
FIG. 15 is a schematic, operational view of the catheter assembly illustrating the anchoring device automatically returning to a low-profile state upon release of a lock.

Ultimately, it will be desirable to retract the catheter 10 from the body cavity. This cannot be accomplished merely by pulling the tube 14 distally, as this only seeks to increase the anchoring characteristics of the catheter 10. Rather, the cap 30 and anchor distal end 26 in this embodiment are released from the distal end proximate position, so that they are free to move distally away from the slide 27 and anchor proximal end 28. Then when removal forces are applied to the tube 14, they push distally on the anchoring device 32 forcing the cap 30 away from the slide 27, thus spacing the anchor distal end 26 further from the anchor proximal end 28. The anchor distal end 26 thus moves from the fixed, distal end proximal position to a released, distal end distal position. These removal forces do not permit the slide 27 to move distally beyond the stop 23. Thus, the removal forces cause the anchor distal end 26 and the anchor proximal end 28 to move to their separated positions, placing the anchoring device 32 in the low-profile state, as shown in FIG. 5. With this low-profile configuration, the catheter 10 can be easily removed in the proximal direction as shown in FIG. 15.

Many different mechanisms can be employed to release the releasable lock 34 sufficiently to permit distal movement of the cap 30 and anchor distal end 26. By way of example, a button or slide can be fixed to the suture 34 at the shaft proximal end 16 of the tube 14. Movement of this slide 27 distally relative to the tube 14 will permit the string 34 and the attached cap 30 to also move distally.

In a preferred method of release, the tubular body 14 is merely cut in two, thereby severing the suture 34 distally of its attachment to the tube 14 or hub 21. If the suture 34 is attached to the hub 21, the tube 14 need only be cut distally of the hub 21. This will release the cap 30 from the shaft distal end 18 of the tube 14 in the manner previously discussed. However, the cap 30 is not free of the catheter 10 as it continues to be attached through the anchoring device 32 to the slide 27 which is constrained by the stop 23.

The cutting of the catheter body 14 and suture 34 is illustrated in FIG. 5, which shows the cap 30 released from the shaft distal end 18 of the tube 14. At this point, distally-directed withdrawal forces cause the slide 27 and anchor proximal end 28 to move against the stop 23 and further cause the cap 30 and anchor distal end 26 to move distally to an extent limited only by the length of the anchoring device 32. With the maximum separation of the cap 30 and the slide 27, resulting in the maximum separation of the anchor distal end 26 and anchor proximal end 28, the anchoring device 32 is maintained in the low-profile state facilitating withdrawal of the catheter 10, as illustrated in FIGS. 7 and 15.

From the foregoing description, it will be apparent that many other types of anchoring devices can also be provided with the self-deploying characteristics of the present invention. For example, an anchoring device can be provided in the form of a Malecot-winged structure 32b, including a plurality of leg pairs each having a living hinge 42, as illustrated in FIG. 6. In this case, the legs 40 of the Malecot structure 32b are attached at one end to the associated living hinge and at the other end, 26 or 28, to either the cap 30 or the slide 27.

The anchor can also be formed as a spiral 32c, as illustrated in FIGS. 7 and 8, with its anchor distal end 26 and the anchor proximal end 28 fixed to the cap 30 and slide 27, respectively. When the opposed ends 26, 28 are brought into close proximity, the spiral 36 moves from its low-profile state, illustrated in FIG. 7, to its high-profile state, illustrated in FIG. 8.

The anchor device in any of the foregoing embodiments can be formed of either plastic or metal materials. While plastic might be the preferred material for the woven mesh bulb, a metal material might be more appropriate for the spiral. Also, as previously noted, the string 34 can be interiorly attached to either the tube 14 or hub 21. In this construction, the catheter 10 is entirely sealed between the shaft proximal end 16 and shaft distal end 18. It remains sealed during insertion and throughout its operative use in the anchored state. The advantageous seal configuration is maintained until the tube 14 is cut and the catheter 10 is removed.

Given the foregoing description of preferred embodiments and method steps, it can be seen that the user of the catheter 10 is merely required to provide a light distal force to insert the catheter 10, a slight proximal force to anchor the catheter 10, and a cutting force to retract the catheter 10. In each of these steps, the tip 12 automatically deploys to the low-profile insertion state, the high-profile anchor state, and the low profile removal state. No additional structure is required, and no further steps of operation or manual manipulation are needed to use this catheter.

A further preferred embodiment of a urinary drainage catheter is illustrated in FIGS. 9-11 are designated by the reference numeral 100. The catheter 100 is representative generally of any medical instrument having an associated tube, or shaft 112 which is adapted for insertion through a body conduit and for anchoring in a body cavity. In the case of the urinary drainage catheter 10, the tube 112 is a catheter body adapted for insertion through the urethra and into the bladder where the catheter 100 can be anchored to facilitate drainage of the bladder.

The tube 112 has a shaft proximal end 114 and a shaft distal end 116, with an anchor assembly 118 having a high-profile state as illustrated in FIG. 10 and a low-profile state as illustrated in FIGS. 9 and 11. The anchoring assembly 118 includes a stop, or block 121 fixed to the tube 112 generally at the position desired for the anchoring assembly 118. Drainage is facilitated by holes 119 and 120 which extend into the tube 112 at the shaft distal end 116.

The anchoring assembly 118 also includes an anchoring device 122 having an anchor proximal end 123 and an anchor distal end 125. In a preferred embodiment, the anchoring assembly 118 includes a proximal bushing 127 and a distal bushing 130 that further defined the anchor proximal end 123 and the anchor distal end 125, respectively. The anchoring device 122 preferably comprises a bulb.

The proximal busing 127 is preferably mounted on the tube 112 proximally of the stop 121, and is movable between a proximal position illustrated generally in FIGS. 10 and 11 by the reference numeral 134, and a distal position illustrated generally in FIG. 9 by the reference numeral 132. Accordingly, the anchor proximal end 123 is movable between a proximal end proximal position 132, shown in FIG. 9, and a proximal end distal position 134, shown in FIGS. 10 and 11.

Similarly, the distal bushing 130 is disposed distally of the block 121 and is movable from a fixed, proximal position illustrated generally in FIGS. 10 and 11 by the reference numeral 136, and a released, distal position illustrated generally in FIG. 14 by the reference numeral 138. Accordingly, the anchor distal end 125 is movable between a fixed, distal end proximal position 136 shown in FIGS. 9 and 10, and a released, distal end distal position 138 shown in FIG. 11.

A releasable locking mechanism 143 is provided to maintain the distal bushing 130 in its proximal position 136. In the illustrated embodiment, this locking mechanism 143 is provided in the form of a tension member such as a suture 143 which extends around the distal bushing 130, through the holes 119 and 120, and through the tube 112 where is fixed at the shaft proximal end 114.

Figure 13:
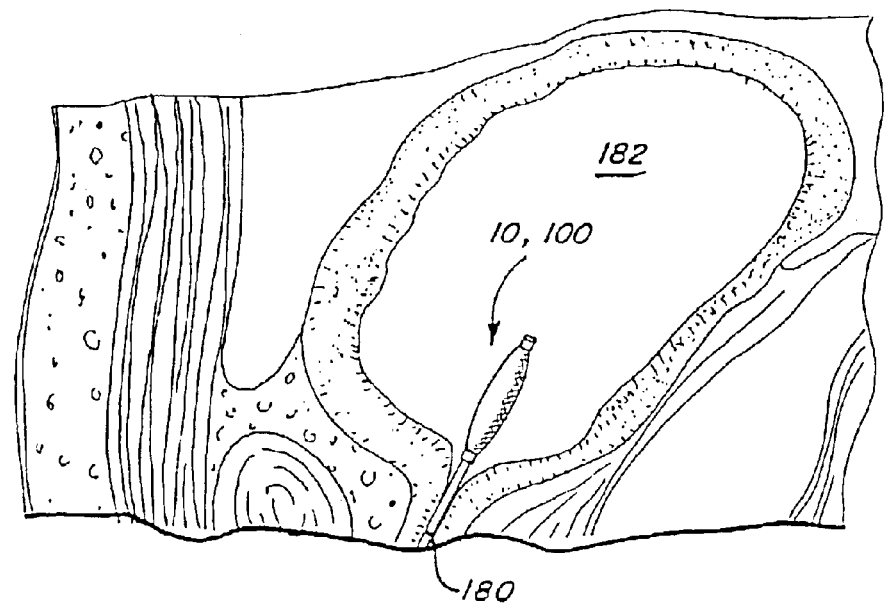
FIG. 13 is a schematic, operational view of the catheter assembly when an anchoring device is fully inserted into the body cavity.

In operation, the tube 112 of the catheter 100 is inserted into the body conduit, such as the urethra as shown in FIGS. 12 and 13. During this insertion step, the distal bushing 130 is locked in its proximate position by the suture, sown in FIG. 9.

Insertion is accomplished by resisting a proximally directed force 144 on the catheter 100 as it is pushed through the body conduit 180. This proximally directed force 144 ends to automatically move the bushings 127 and 130 to their proximal positions. As illustrated in FIG. 9, the distal bushing 130 cannot move proximally of the stop 121, so further movement of the proximal bushing 127 proximally operates to separate the anchor ends 123 and 125 of the anchoring device 122 causing it to maintain a low-profile state. This low-profile state, which occurs automatically, greatly, facilitates insertion of the catheter 100 through the body conduit 180, such as the urethra, and into the body cavity 182, such as the bladder. In FIG. 13, this insertion continues preferably until the proximal bushing 127 passes into the body cavity.

At this point, the catheter 100 can be withdrawn slightly thereby creating a distally directed force 145 shown in FIG. 14. This force 145 is initially directed against the proximal bushing 127 causing it to move to its distal position 134, as shown in FIG. 10. With the distal bushing 130 locked in its proximal position 136, distal movement of the busing 127 causes the anchoring device 122 to move toward its high-profile state as illustrated in FIG. 14. Further withdrawal of the catheter 100, either accidentally or intentionally, is inhibited by the high profile of the anchoring device 22.

Although the distally directed force 14t against the anchoring device 122 would tend to cause the distal bushing 130 to move distally, it is maintained in its proximal position by the locking mechanism 143 in the form of the suture. In this anchored state shown in FIG. 14, the catheter 100 can remain for an indefinite period of time in body cavity 182, such as the bladder.

When it is desirable to remove the catheter 100 from the body cavity, the locking mechanism 143 must be released or disengaged. In an embodiment including the suture 143 as shown in FIG. 9, this release can be facilitated by merely cutting the tube 112 of the catheter 100 at the proximal end 114. This will disengage the suture 143 from the shaft 112 and thereby release the distal bushing 130 for movement to its distal position 138 as illustrated in FIGS. 11 and 15.

Retraction of the catheter 100 again applies the distally directed force 145 to the anchor assembly 118. With the bushing 127 already in its distal position 134, the force 145 is now applied directly to the anchoring device 122 ad ultimately to the distal bushing 130. Since the proximal busing 127 cannot move distally of the stop 121, movement of the distal bushing 130 to its distal position 138 elongates the anchoring device 122 automatically placing it in its low-profile state and facilitating withdrawal of the catheter 100, as shown in FIGS. 11 and 15.

Operation of this anchoring mechanism 118 is optimized for a semi-permanent/implantable drainage catheter for several reasons. First, it maximizes the drainage internal diameter of the tube 112 because the anchoring mechanism 118 can rely on memory characteristics of the bulb 122 for its deployment. There is no need for a space-consuming inflation lumen or activation rod in the internal diameter of the tube 112. All that is required to occupy the lumen is a relatively small tension member, such as the suture 143.

Second, the fact that the tension member is provided in the form of the suture 143 is advantageous not only because it is small but also because it is very flexible. This allows the catheter to more easily follow the contours of the body conduit without interference between the tension member and the natural geometry of the body.

Third, the activation and deactivation of the anchor mechanism 118 is "automatic". There is no need for a stylet or introducer sheath to facilitate either insertion or withdrawal of the catheter. There is no need for manual tensioning of the suture as in devices of the past. Furthermore, the deactivation feature requires only the severing of the tube 112 by any available means. This simplicity of activation provides a significant advantage particularly in the case of a urinary drainage catheter. No need exists for a sterile syringe, water or sterile mandrel as required by current urinary drainage catheters.

Fourth, the anchoring mechanism 118 maximizes the strength of the anchoring device 122 because it allows for a "solid length" or "stacked" configuration to be achieved. The device could be easily designed with a fail-safe break strength in the tension member so that accidental removal attempts would undeploy the retention feature before its high profile in any way harmed the anatomy.

This design would also be well suited for drainage anywhere a catheter is introduced into natural cavities of the body such as the bladder, urethra, ureters, kidneys, lungs, etc., or into accidental or surgically-made cavities, for the purpose of evacuating liquid secretions which are not expelled in the normal manner. The device possesses a high degree of flexibility while maintaining itself permanently in position without extraneous means of attachment or fixation.

Alternate versions of the drainage device could be made. For example, the design does not have to be flexible. A version with a stiff tube or a stiff tension member would work if it were not necessary to follow a torturous body contour. A rigid preformed device would work as well as a straight version, for example if the device needed to have the general shape of an arc.

The device could be made in a variety of sizes. For instance, a relatively larger size for urine drainage or a relatively smaller size to anchor in the cystic ducts. Likewise, the anchoring device 122 could be extremely porous for urine drainage or made with a water tight coating for a cholangeogram-type device.

The anchoring assembly 118 is well suited for retaining the position of laparoscopic trocars or instrumentation. Additionally, the retention feature could also be incorporated in Hand Assist Ports to anchor them in position. Furthermore, a version of the assembly 118 may be well suited as a "mechanical balloon" for clot or stone removal.

Although the anchoring mechanism 118 as described above preferably includes the bulb 122, this structure is merely representative of many other types of structures which might be advantageously incorporated in a particular embodiment. In general, the anchoring device 122 has a pair of ends, the proximity of which determine whether the structure has a high profile or a low profile. This bulb 122 might be replaced by a spiral structure or a Malecot-winged structure. Furthermore, the bulb 122 and its equivalents are not necessarily required to be coaxial with the shaft 112 in order to accomplish its anchoring function.

In the embodiment disclosed above, the locking mechanism 143 is described to include a suture. Certainly there are other methods and apparatus which could releasably lock the distal bushing or cap in its proximal position. Basically, any structure removably present in the path of the distal bushing or cap could perform this function. The retaining object could be removed from the path of the bushing 130 by a rod or even hydraulics applied through the tube 112.

An anchor strap is illustrated in FIG. 16 and designated by the reference numeral 125. In this view, the strap 125 is illustrated with a straight configuration to show a distal tip, a proximal end, and a pair of large slots formed along the strap between these two ends. The distal tip extends in a generally parabolic configuration laterally of the plane of the strap 125. A channel is provided along the axis of this parabolic tip. In a preferred embodiment, the strap 125 is formed of a heatset or thermoset material and provided with a serpentine configuration as illustrated in FIG. 17.

A catheter body is illustrated in FIG. 18 and designated with a reference numeral 127. This catheter body has a generally cylindrical and tubular configuration with a plurality of drainage holes cut through the walls of the body 127 and communicating with an axial lumen at the distal end of the catheter body 127.

As illustrated in FIG. 19, the anchor strap 125 can be attached to the catheter body 127 by two pieces of suture material designated by the reference numerals 129 and 131. Notably, in this embodiment these are the only four elements of structure associated with the operative end of the drainage catheter. This simplicity of structure and low cost manufacture is of particular advantage to this embodiment.

The manufacturing steps begin by threading the catheter body 127 through the slots in the anchor strap 125 as illustrated in FIG. 19. The suture 129 can then be threaded through the distal most drainage hole in the catheter body 127, as well as the channel in the distal tip of the anchor strap, for example, as illustrated in the enlarged view of FIG. 20. The ends of the suture material 129 can be threaded proximally through the lumen of the catheter body 127 for ultimate access at the proximal end of the catheter body. Maintaining tension on the ends of the suture material 129 fixes the distal tip of the anchor strap to the distal end of the catheter body 127 as illustrated in FIG. 19.

The separate piece of suture material 131 illustrated in FIG. 21 can be used to attach the proximal end of the anchor strap to the catheter body 127. In the illustrated embodiment, the suture material 131 is threaded through the proximal slot in the anchor strap as well as drainage holes in the catheter body 127.

Operation of the drainage catheter is illustrated in the progressive views of FIGS. 22-25. In FIG. 22, the catheter is illustrated during an insertion step. In this step, the anchor strap one is compressed against the catheter body 127 providing the strap 125 with an elongated narrow configuration. Once the catheter is in place and the anchor strap is no longer restricted, the strap will automatically tend to assume its thermoset serpentine configuration. Any proximal force applied to the catheter at this time will only serve to increase the size of the anchor strap 125 as illustrated in FIG. 23.

Once the catheter has served its purpose, the anchor strap 125 can be partially separated from the catheter body by merely severing or releasing the ends of the suture 129 at the proximal end of the catheter. This will release the parabolic distal tip of the anchor strap 125 from the catheter body 127, as illustrated in FIG. 24.

When the catheter is withdrawn as illustrated in FIG. 25, the suture 131 will cause the anchor strap 125 to follow the catheter body 127. As the anchor strap 125 is drawn into the tissue canal, it will automatically deploy into a straight configuration providing a low profile as it is withdrawn.

Again, it will be noted that this operative end of the drainage catheter may include only two primary elements, the catheter body 127 and the anchor strap 125. With the addition of two pieces of suture material 129 and 131, the anchor strap can be fixed to the catheter shaft 127 for simple and atraumatic insertion. Notwithstanding the narrow configuration achieved upon insertion, the anchor can deploy to a significant size so that it easily functions to anchor the distal end of the catheter. Drainage holes are provided very close to the distal end of the catheter shaft 127, thereby facilitating complete drainage of the bladder. By simply releasing or cutting one of the sutures, the anchor can be partially separated from the catheter body to facilitate an elongate simple withdrawal of the catheter body 127 followed by the anchor strap 125.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what incorporates the essential idea of the invention.

What is claimed is:

1. A catheter, comprising:

an elongate tube having a proximal end and a distal end;

an anchor disposed generally at the distal end of the tube and being moveable between an insertion position and a withdrawal position relative to the tube, the anchor in the Insertion position having a low profile when the tube is moved distally, the anchor in the withdrawal position having a low profile when the tube is moved proximally, the anchor in the insertion position having a high profile when the tube is moved proximally, said anchor further comprising a cap being movable relative to the tube to permit the anchor to move from the insertion position to the withdrawal position; and a tension element attached to the cap for releasable holding the anchor in a fixed relationship with the tube.

2. The catheter recited in claim 1, wherein the tension element has properties facilitating separation of the tension element to enable a space relationship between the tube and the cap in the withdrawal position.

3. A catheter, comprising:

an elongate tube having a proximal end and a distal end;

an anchor disposed of the distal end of the tube, the anchor having a first end and a second end;

means for attaching the first end of the anchor to the tube;

a tension member extending distally of the tube for releasably holding the second end of the anchor in a fixed relationship with the tube.

4. The catheter recited in claim 3, wherein:

the anchor has the insertion state and a withdrawal state;

the first end of the anchor has a floating relationship with the tube in the insertion state; and the second end of the anchor has a floating relationship with the tube in the withdrawal state.

5. The catheter recited in claim 3, wherein:

the anchor has a high-profile state when the first end of the anchor has a proximate relationship with the second end of the anchor and the anchor lies a tow-profile state when the first end of the anchor has a spaced relationship with the second end of the anchor.

6. The catheter recited in claim 3, further comprising a stop included in the attaching means and having a fixed relationship with the tube.

7. The catheter recited in claim 3, wherein the attaching means comprises a tension member.

8. The catheter incited in claim 7, wherein the tension member extends between the first end of the anchor in a position in proximity to the proximal end of the tube.

9. The catheter recited in claim 8, wherein the tension member is severable to release the second end of the anchor from the fixed relationship with the tube.

10. A method for withdrawing a catheter anchored through a body conduit in a body cavity, comprising the steps of:

providing the catheter with an elongate tube having an anchor at a distal end of the tube, the anchor having a distal tip held in proximity to the distal end of the tube by a tension element extending away from the distal end of the tube; and severing the tension element to release the distal tip of the anchor from the tube.

11. The method recited in claim 10, wherein the tube has a proximal end and the severing step further comprises the step of:

cutting the tension element in proximity to the proximal end of the tube.

12. The method recited in claim 10, further comprising the step of: attaching the anchor to the tube at other than the distal tip of the anchor.

13. The method recited in claim 10, further comprising the step of:

withdrawing the tube and the anchor from the body cavity and through the body conduit in a low-profile state.

* * * * *

UNITED STATES PATENT AND TRADEMARK OFFICE
CERTIFICATE OF CORRECTION

| | |
|---|---|
| PATENT NO. | : 6,837,871 B2 |
| APPLICATION NO. | : 10/403758 |
| DATED | : January 4, 2005 |
| INVENTOR(S) | : Joseph A. Gonzales and Bouon Pravong |

It is certified that error appears in the above-identified patent and that said Letters Patent is hereby corrected as shown below:

In Claim 1, column 14, line 59, please delete the word "Insertion" and replace with the word --insertion--.

In Claim 1, column 15, line 1, please delete the word "releasable" and replace with the word --releasably--.

In Claim 5, column 15, line 22, please delete "anchor" and replace with --anchor;--.

In Claim 5, column 15, line 23, please delete "lies a tow-profile" and replace with --has a low-profile--.

Signed and Sealed this

Thirty-first Day of January, 2012

David J. Kappos
*Director of the United States Patent and Trademark Office*